US00PP08682P

United States Patent [19]

Austin

[11] Patent Number: Plant 8,682

[45] Date of Patent: Apr. 12, 1994

[54] ROSE PLANT 'AUSBREAK'

[75] Inventor: David C. H. Austin, Albrighton, England

[73] Assignee: David Austin Roses Limited, Albrighton, England

[21] Appl. No.: 955,912

[22] Filed: Sep. 30, 1992

[51] Int. Cl.[5] ..... A01H 5/00

[52] U.S. Cl. ..... Plt./1

[58] Field of Search ..... Plt. 1, 24

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A shrub rose variety having paler colored flowers than parents, hang taller and more sturdy than the variety Tamora, with flowers flatter and more quartered than parents, and with highly scented flowers.

1 Drawing Sheet

The present invention relates to a new and distinct variety of shrub rose plant of the Rosa hybrida class which was originated by me by crossing the variety Graham Thomas, with the variety Tamora.

The primary objective of this breeding was to produce a new rose variety having yellow, quartered, scented flowers on a bushy plant which repeatedly flowers. The objective was substantially achieved along with other desirable improvements as evidenced by the following unique combination of characteristics which are outstanding in the new variety and which distinguish it from its parents, as well as from all other varieties of which I an aware:

1. Paler colored flowers than parents;
2. Taller and more sturdy than Tamora;
3. Flowers flatter and more quartered than parents; and
4. Highly scented.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Graham Thomas.

*Pollen parent.*—Tamora.

Classification:

*Botanical.*—Rosa hybrida.

*Commercial.*—Shrub.

FLOWER

Observations made from specimens grown in a garden environment in Albrighton, Wolverhampton, England, in August, 1991.

Blooming habit: Recurrent.

Bud:

*Size.*—About 1" long when the petals start to unfurl.

*Form.*—The bud form is medium, globular with long cuspidate apex.

*Color.*—When sepals first divide, the bud color is brownish red 8C6. When half blown, the upper and lower sides of the petals are pale yellow 3A3, yellow 3A5 at base.

*Sepals.*—Color: Greyish green 29D to E7. Surface texture: Leathery, slightly grainy. There are three normally appendaged sepals. There are two unappendaged sepals with hairy edges.

*Receptacle.*—Color: Deep green 9D8. Shape: Goblet shaped. Size: Medium, small, about $\frac{3}{8}'' \times \frac{1}{4}''$. Surface: Smooth.

*Peduncle.*—Length: Medium, averaging about $1\frac{3}{4}$-$2\frac{3}{4}''$. Surface: Glandular. Color: Light green, bronzy, 30D7 and brownish violet blush 11D7. Strength: Erect.

Bloom:

*Size.*—Medium. Average open size is $2\frac{1}{2}$-$3\frac{1}{4}''$.

*Borne.*—Singly and several together in clusters of up to 6 flowers irregular shape.

*Stems.*—Average length is from 24 to 30 inches.

*Form.*—When first open: Cupped. Permanence: Flattens, outer petal edges curl slightly.

*Petalage.*—Number of petals under normal conditions: 70 to 100.

*Color.*—The upper side of the petals is yellow 2A5 to 4A3. The reverse side of the petals is yellow 2A5 to 4A3. The color of the base of the petals is yellow 3A6. The major color on the upper side is yellow 4A3.

*Variegations.*—None.

*Discoloration.*—The general tonality at the end of the first day: Very slightly faded. At the end of the third day, pink/white 7A2 to pale yellow 3A3.

*Fragrance.*—Strong and musky.

Petals:

*Texture.*—Sheeny, thick.

*Shape.*—Round, heart-shaped.

*Form.*—Cupped.

*Arrangement.*—Quartered. Inner petals caught into calyx to form a button, with few petaloids in the center.

*Persistence.*—Medium. Petals hang on and dry.

*Lastingness.*—On the plant: Long, about 7 to 10 days. As a cut flower: About 4 to 7 days.

Reproductive parts:

*Anthers.*—Size: Medium. Quantity: Few (5-35). Color: Yellow. Arrangement: Tucked in calyx or partly so.

*Filaments.*—Color: Yellow.

*Pollen.*—Color: Gold yellow.

*Styles.*—Color: Pale green 30A3.

*Stigmas.*—Color: Yellow, with cerise 12C8 streak at base.

Form: Shrub.

Growth: Medium, branching.

Height: 42 inches.

Foliage: Number of leaflets on normal mid-stem leaves: 5.

*Size.*—Medium, about 1¾" long.

*Quantity.*—Normal.

*Color.*—New foliage: Deep green 29E8. Old foliage: Dark green 28F7.

Leaflets:

*Shape.*—Base is round, oval. Tip is pointed.

*Texture.*—Upper side: Leathery.

*Edge.*—Serrated.

*Serration.*—Single, small.

*Petiole rachis.*—Color: Green, reddish 30E8 with violet brown 11D7 tinge.

*Petiole underside.*—With prickles, 1 to 3 per internode.

*Stipules.*—Medium, serrated, about ¾" long and glandular.

*Disease resistance.*—Resistant to mildew and blackspot under normal growing conditions at Albrighton, Wolverhampton, England.

Wood:

*New wood.*—Color: Parrot green 30E8. Bark: Smooth.

*Old wood.*—Color: Green, deep green 29E8. Bark: Smooth.

Prickles:

*Quantity.*—On main canes from base: Ordinary. On laterals from main canes: Ordinary to few.

*Form.*—Medium, straight.

*Color when young.*—Red, brown, rosewood 9D5.

*Position.*—Evenly spaced along stem.

Small Prickles:

*Quantity.*—On main stalks: None. On laterals: None.

I claim:

1. A new and distinct variety of shrub rose plant of the Rosa hybrida class, substantially as herein shown and described, characterized particularly as to novelty by the unique combination of its having paler colored flowers than its parents, its being taller and more sturdy than the variety Tamora, flowers flatter and more quartered than parents, and highly scented flowers.

* * * * *

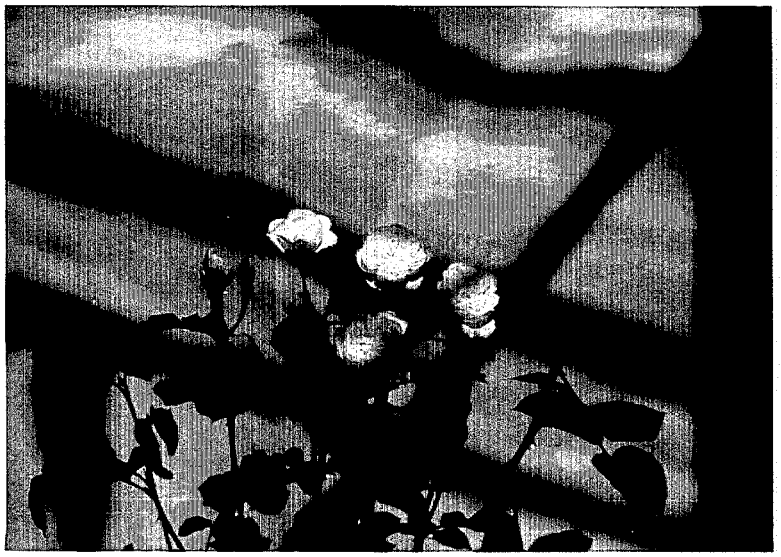

UNITED STATES PATENT AND TRADEMARK OFFICE

CERTIFICATE OF CORRECTION

PATENT NO. : PP 8,682

DATED : April 12, 1994

INVENTOR(S) : David Charles Henshaw Austin

It is certified that error appears in the above-identified patent and that said Letters Patent is hereby corrected as shown below:

Title page, item [57], Abstract, line 2, "hang" should be --being--;

column 2, line 14, "9D8" should be --29D8--;

column 2, line 22, "2½-3¼"" should be --2½-3¼" in diameter--;

column 2, line 24, "flowers irregular" should be --flowers of irregular--; and column 2, line 29, "70 to 100" should be --average 70 to 100--.

Signed and Sealed this

First Day of November, 1994

Bruce Lehman

*Attest:*

BRUCE LEHMAN

*Attesting Officer*

*Commissioner of Patents and Trademarks*